United States Patent [19]

Kaplan et al.

[11] 4,064,345

[45] * Dec. 20, 1977

[54] CEPHALOSPORINS DERIVATIVES 7-CYCLIZED α-AMINO-3-HETEROTHIO

[75] Inventors: Murray A. Kaplan, Syracuse; William J. Gottstein, Fayetteville; Alphonse P. Granatek, Baldwinsville, all of N.Y.

[73] Assignee: Bristol-Myers Company, New York, N.Y.

[*] Notice: The portion of the term of this patent subsequent to Dec. 6, 1994, has been disclaimed.

[21] Appl. No.: 745,034

[22] Filed: Nov. 26, 1976

Related U.S. Application Data

[62] Division of Ser. No. 640,317, Dec. 12, 1975, abandoned.

[51] Int. Cl.$^2$ .................................. C07D 501/36
[52] U.S. Cl. .................................. 544/27; 424/246
[58] Field of Search .................................. 260/243 C

[56] References Cited

U.S. PATENT DOCUMENTS

| | | | |
|---|---|---|---|
| 3,303,193 | 2/1967 | Godfrey | 260/243 C |
| 3,489,751 | 1/1970 | Crast | 260/243 C |
| 3,912,728 | 10/1975 | Crooij et al. | 260/243 C |

Primary Examiner—Nicholas S. Rizzo
Assistant Examiner—David E. Wheeler
Attorney, Agent, or Firm—Herbert W. Taylor, Jr.

[57] ABSTRACT

Compounds of the formula

I

-continued

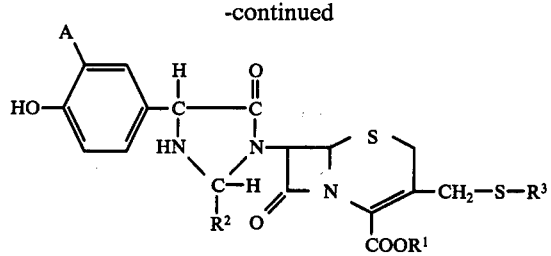

wherein
A is hydrogen, hydroxy, methyl or methoxy,
R$^1$ is hydrogen, sodium or potassium,
R$^2$ is carboxyl or 2-furyl or an aliphatic, aromatic or heterocyclic radical to which there is also attached a strongly acidic group in the form of its sodium or potassium salt, and
R$^3$ is tetrazol-5-yl, 1,2,4-thiadiazol-5-yl, 1,3,4-thiadiazol-2-yl, 1,3,4-oxadiazol-3-yl or 1,2,4-triazol-5-yl, each of such groups being unsubstituted or substituted with one or two lower alkyl groups of one to four carbon atoms are prepared by reacting the appropriate aldehyde with the corresponding amphoteric cephalosporin. Preferred products have the structure

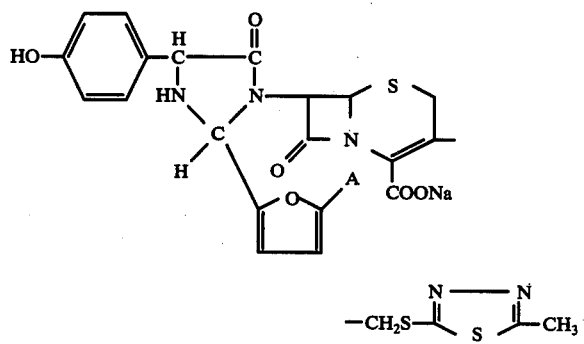

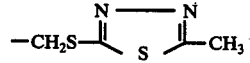

in which A is —H or —SO$_3$Na.

31 Claims, No Drawings

CEPHALOSPORINS DERIVATIVES 7-CYCLIZED α-AMINO-3-HETEROTHIO

CROSS REFERENCE TO RELATED APPLICATION

This application is a division of our prior copending application Ser. No. 640,317 filed Dec. 12, 1975, now abandoned.

BACKGROUND OF THE INVENTION

1. Field of the Invention

The cephalosporin derivatives of the present invention possess in general the usual attributes of that family of antibacterial agents and are particularly useful in the treatment of bacterial infections by injection.

2. Description of the Prior Art

Derivatives of various α-amino penicillins and cephalosporins with nitro-substituted heterocyclic aldehydes are described in U.K. Pat. No. 1,311,498. Reaction products of various α-amino penicillins and/or cephalosporins with formaldehyde are disclosed in South African Pat. No. 72/8475 (see U.K. Pat. No. 1,401,285), with acetaldehyde in South African Pat. No. 72/8474 (See U.K. Pat. No. 1,389,540) and with various aldehydes and ketones in South African Pat. No. 72/8476 (See U.K. Pat. No. 1,388,400).

Derivatives of cephalosporins having in the acylamido group at the 7-position an α-amino group which has been reacted with an aldehyde are disclosed in U.S. Pat. No. 3,880,842; U.S. Pat. No. 3,887,546 and Farmdoc 49804W.

The reaction products of acetone with various α-amino cephalosporins are disclosed in the patent literature as follows:

1. with cephaloglycin, in U.S. Pat. No. 3,303,193;
2. with cephalexin, in U.S. Pat. No. 3,714,146 and U.K. Pat. No. 1,314,758 and U.S. Pat. No. 3,780,028;
3. with 7-[α-amino-(2'-thienyl)acetamido]-cephalosporanic acid, in U.S. Pat. No. 3,311,621;
4. with certain ring-substituted cephaloglycins in U.S. Pat. No. 3,464,985; and
5. with certain ring-substituted cephalexins and cephaloglycins, in U.S. Pat. Nos. 3,489,750; 3,489,751 and 3,489,752.

More distantly related are the intermediates produced when a cephalosporin nucleus, e.g. 7-ACA or 7-ADCA, is acylated with a reactive derivative of an α-amino acid in which the α-amino group has been protected by prior reaction with a β-diketo compound such as methyl acetoacetate, methyl acetoacetamide or acetylacetone; these are exemplified by Farmdoc 22850W and 60669V.

In the penicillin field the penicillins containing an α-amino group in the 7-acylamido substituent, e.g. ampicillin, with ketones and aldehydes were apparently first disclosed by Johnson et al. (U.S. Pat. No. 3,198,804) and Granatek (U.S. Pat. No. 3,198,788). Similar reaction products made from various such penicillins by reaction with the same or different aldehydes and ketones were later reported in U.S. Pat. Nos. 3,230,214, 3,316,247 (diketones), 3,325,479 (diketones), 3,489,746, 3,549,746, 3,558,602, 3,635,953, 3,641,000, 3,647,781 (which includes some cephalosporins), 3,725,389, 3,780,028 3,784,562 (diketone), 3,886,140, 3,888,848, 3,905,955 and 3,904,604 and U.K. Pat. No. 1,267,936.

SUMMARY OF THE INVENTION

At its broadest the present invention provides the condensation products of aldehydes other than formaldehyde and acetaldehyde with 3-thiolated-cephalosporins having at the 7-position an α-aminophenylacetamido substituent which can be unsubstituted in the benzene ring or substituted with one, two or three groups which are unreactive toward aldehydes and preferably with a para-hydroxy or a para-acetoxy group. By "3-thiolated-cephalosporin" is mean a derivative of cephalosporanic acid in which the acetoxy group has been displaced by a thiol to convert the 3-acetoxymethyl group to a 3-(substituted)-thiomethyl group; preferred thiols are those in which the mercapto group is attached to a carbon atom in a 5- or 6-membered heterocyclic ring containing 1–4 (and preferably 3 or 4) N—, O— or S— atoms, said ring being optionally substituted with one or two alkyl or alkoxy groups containing 1 to 4 carbon atoms, methylthio or trifluoromethyl.

The resulting condensation products in the form of their sodium and potassium salts exhibit desirable solubility, stability and absorption. The preferred species hydrolyze rapidly and completely in the body to regenerate the original amphoteric 3-thiolated cephalosporin.

There is thus provided the sodium or potassium salt of the equimolar condensation product of (a) an aldehyde other than formaldehyde or acetaldehyde with (b) an amphoteric 3-thiolated cephalosporin containing an α-substituted-α-aminoacetamido group at the 7-position and having in its zwitterion form an aqueous solubility of less than 125 mgm./ml. and in a preferred embodiment there is provided the sodium or potassium salt of the equimolar condensation product of (a) an aldehyde having the formula $R^2$—CHO wherein $R^2$ is carboxyl or 2-furyl or an aliphatic, aromatic or heterocyclic radical to which there is also attached a strongly acidic group in the form of its sodium or potassium salt with (b) an amphoteric 3-thiolated cephalosporin containing an α-substituted-α-aminoacetamido group at the 7-position and having in its zwitterion form an aqueous solubility of less than 125 mgm./ml.; in a narrower preferred embodiment the aldehyde bearing the acidic group is 5-formyl-2-furansulfonic acid, o-benzaldehyde sulfonic acid, 4-methoxybenzaldehyde-3-sulfonic acid, 4-hydroxybenzaldehyde-3-sulfonic acid, o- and p-formylphenoxyacetic acid, 5-formyl-salicylic acid, p-formylcinnamic acid, glyoxalic acid, phthalaldehydic acid, p-formyl-benzoic acid, acetaldehyde sulfonic acid sodium salt or acetaldehyde disulfonic acid sodium salt.

The present invention provides the compounds of the formula

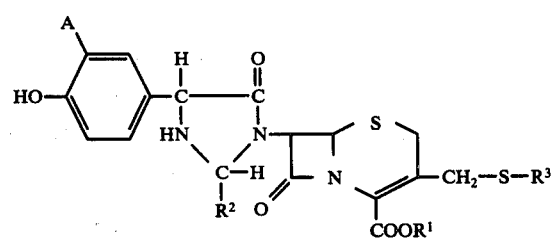

I wherein
A is hydrogen, hydroxy, methyl or methoxy,
$R^1$ is hydrogen, sodium or potassium, R[2] is carboxyl or 2-furyl or an aliphatic, aromatic or heterocyclic radical to which there is also attached a strongly acidic group in the form of its sodium or potassium salt, and R[3] is tetrazol-5-yl, 1,2,4-thiadiazol-5-yl, 1,3,4-thiadiazol-2-yl, 1,3,4-oxadiazol-3-yl or 1,2,4-triazol-5-yl, each of such groups being unsubstituted or substituted with one or two lower alkyl groups of one to four carbon atoms. In the preferred embodiments the carbon atom attached to the benzene ring (para to the hydroxyl group) has the D configuration.

The present invention thus provides watersoluble, pharmaceutically acceptable derivatives of the amphoteric cephalosporins having the structure

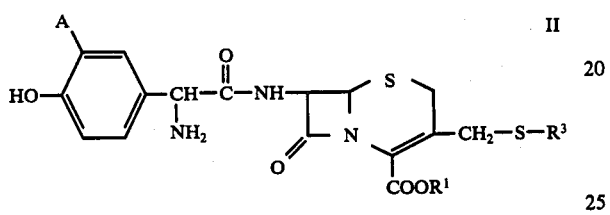

II wherein A, R[1] and R[3] have the meaning set forth above. In the preferred embodiment the carbon bearing the α-amino group has the D configuration. These tare derivatives which (1) upon the addition of water will give true solutions for parenteral administration, (2) have acceptable thermal stability in the solid state, (3) in aqueous solution have a useful life of at least several hours at room temperature and (4) on intravenous or intramuscular injection result in little or no muscle or vein irritation. More particularly, the present invention provides alkali metal salts, especially sodium and potassium salts, of the reaction products of said amphoteric cephalosporins with aldehydes and preferably with furfuraldehyde or an aldehyde containing an acidic group, e.g. 2-furansulfonic acid.

The compounds of the present invention exhibit desirable solubility, stability and absorption. The preferred species hydrolyze rapidly and completely in the body to regenerate the original amphoteric cephalosporin of formula II. The compounds of the present invention thus overcome the problems posed by the instability to high pH and frequency relative insolubility in their zwitterion form of the amphoteric cephalosporins of formula II.

In the preferred embodiments of the present invention the aldehyde with an acidic function is selected from the group consisting of

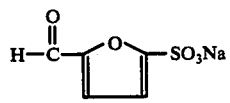

5-formyl-2-furansulfonic acid sodium salt,

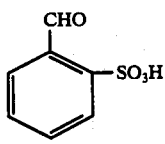

o-benzaldehyde sulfonic acid,

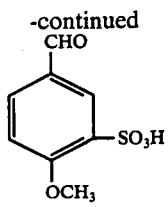

4-methoxybenzaldehyde-3-sulfonic acid,

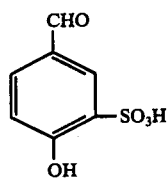

4-hydroxybenzaldehyde-3-sulfonic acid,

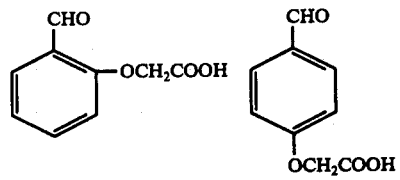

o- and p-formylphenoxyacetic acid,

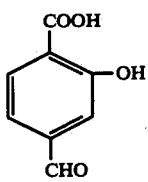

5-formyl-salicylic acid,

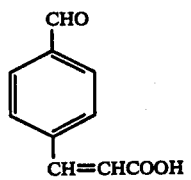

p-formyl-cinnamic acid,

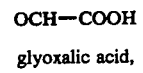

glyoxalic acid,

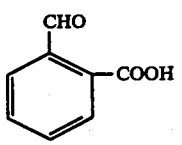

phthalaldehydic acid,

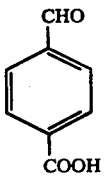

p-formyl-benzoic acid,

acetaldehyde sulfonic acid sodium salt and

acetaldehyde disulfonic acid sodium salt.

Further preferred embodiments of the present invention are those of formula I wherein A is hydrogen, $R^2$ is derived from one of the aldehydes named above and most preferably is

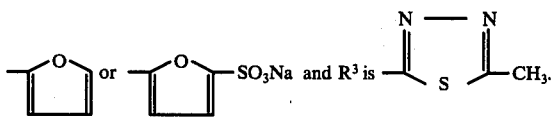

The compounds of the present invention solve the problem of formulating relatively water-insoluble (less than 125 mgm./ml.) amphoteric 3-thiolated cephalosporins for intravenous injection which requires true solutions having a concentration of about 250mgm. in only 1 to 2 milliliters for bolus injection. In addition, such a dosage form can be distributed as a dry-fill (bottle of powder only) which is reconstituted just before use by the addition of sterile water but at that time it must also dissolve completely in a matter of a few minutes to be practical for such use.

In addition, when added (after such reconstitution) to a larger volume of infusion fluid for intravenous drip to give a concentration in the range of 10–25 mgm./ml., the compound must not lose more than 10% of its bioactivity over the 4–6 hours required for the infusion.

Amphoteric 3-thiolated cephalosporins having in their zwitterion form an aqueous solubility of less than about 125 mgm./ml. are clearly not suitable and in addition (unlike their non-amphoteric counterparts such as cephalothin etc.) usually cannot be converted to ordinary, soluble sodium salts because the pH required is so high it causes decomposition and in addition the free amino group existing at that pH is thought to catalyze decomposition.

There is also provided by the present invention a process for the preparation of a compound of the formula

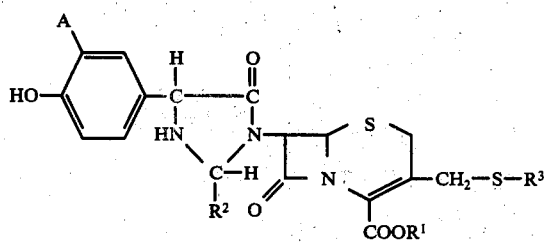

wherein
A is hydrogen, hydroxy, methyl or methoxy,
$R^1$ is hydrogen, sodium or potassium,
$R^2$ is carboxyl or 2-furyl or an aliphatic, aromatic or heterocyclic radical to which there is also attached a strongly acidic group in the form of its sodium or potassium salt, and
$R^3$ is tetrazol-5-yl, 1,2,4-thiadiazol-5-yl, 1,3,4-thiadiazol-2-yl, 1,3,4-oxadiazol-3-yl or 1,2,4-triazol-5-yl, each of such groups being unsubstituted or substituted with one or two lower alkyl groups of one to four carbon atoms which comprises
1. treating an aqueous suspension of an amphoteric cephalosporin of formula II or a solvate or hydrate thereof with an aldehyde having the formula $R^2CHO$ wherein $R^2$ is an defined above and sufficient water-soluble sodium or potassium base to raise the pH of the reaction mixture to between about 5.5 and 8 and preferably pH 6.2–7.2 and to form in solution the desired compound I; and
2. recovering from that solution said compound.

The compounds of formula I have an asymmetric center at the carbon attached to two nitrogen atoms. Thus, compounds of formula I may exist in the form of the DL mixture or as the individual D or L isomers.

The starting material cephalosporin used in Step (1) of the above process may be any form of the amphoteric cephalosporin of formula II including the free acid zwitterion or a hydrate or solvate of said zwitterion.

The concentration of amphoteric cephalosporin starting material is not critical, and good results have been obtained with concentrations between about 25–300 milligrams cephalosporin starting material per milliliter of solvent. The starting material is preferably ground and screened to a finely divided state, most preferably ground to a particle size of less than 200 mesh, so as to increase the surface area and rate of reaction.

The amphoteric cephalosporin starting material is slurried in water to form an aqueous suspension. An alternative to using an aqueous suspension in Step (1) would be to suspend the cephalosporin starting material in an organic solvent which is (1) a solvent for the alkali metal salt end-product, (2) miscible with the aldehyde, (3) chemically inert toward the cephalosporin starting material and end-product and (4) easily removable from the end-product as by mild drying. Examples of organic solvents which might be employed are dimethylsulfoxide and dimethylformamide. Because of the difficulty of removing residual organic solvent from the alkali metal salt end-product, however, the starting material is preferably provided as an aqueous suspension.

After obtaining the cephalosporin starting material in suspension, the desired alkali metal salt of formula I is formed in solution by addition of the aldehyde and an amount of water-soluble alkali metal base, preferably a sodium or potassium base, sufficient to raise the pH of the reaction mixture to between about 5.5 and 8. As the pH is raised to within this range the alkali metal salt of the reaction product of the amphoteric cephalosporin and the aldehyde is formed and goes into solution.

The temperature at which Step (1) is carried out is not critical. The reaction can be performed at room temperature; but higher or lower temperatures may be used and temperatures in the range of 50°–60° C. are preferred.

About 1 mole of the aldehyde is needed per mole of cephalosporin starting material but the aldehyde is preferably added somewhat in excess of the theoretical amount needed so as to ensure complete reaction, i.e. a slight molar excess. The most preferred ratio of aldehyde to cephalosporin starting material is about 1.3–1.4:1.

The alkali metal base may be any water soluble base capable of (1) providing alkali metal cations, preferably sodium or potassium ions, and (2) raising the pH of the reaction mixture to between about 5.5 and 8, most preferably about 6.2 to 7.2. Preferred bases because of their desirable solubility properties are sodium or potassium hydroxide. The $R^3$—S— moiety of compound I may split off at high pH. For this reason the base is added to the reaction mixture in such a manner that the pH is not allowed to rise above about 8. Preferably the base is used in the form of an aqueous solution and is added slowly to the reaction mixture with stirring until the reaction is shown to be complete by pH measurement and by formation of a solution or near solution. The amount of base used is not critical, but preferably about 1 mole of base is used per mole of cephalosporin starting material.

For best results the solution obtained at the conclusion of Step (1) is filtered to remove solid impurities prior to the recovery Step (2). Before filtration, the solution may optionally be carbon-treated with activated carbon to assist in removal of any colored impurities.

The desired product of formula I is then recovered from aqueous or non-aqueous solution as by precipitation or lyophilization. Precipitation of the alkali metal salt may be effected by addition of an organic solvent in which the desired salt is insoluble, i.e. an antisolvent. Examples of such antisolvents include isopropanol, n-propanol, t-butanol and acetonitrile.

The solvent to be used in the precipitation step should be one which can be easily removed from the end-product under conditions which will not result in any significant decomposition of the alkali metal salt. The most preferred antisolvent is isopropanol. The antisolvent may be added to the solution resulting from Step (1) or, alternatively and preferably, the solution containing the desired alkali metal salt is added with stirring to a large excess of the antisolvent. The alkali metal salt of formula I is then recovered by filtration, washed with a suitable organic solvent, e.g. isopropanol, and dried by conventional procedures, e.g. vacuum-drying at 50°–56° C. for 24–48 hours or air drying at 60° C. for 48 hours. As an alternative procedure to recovering the end-product by precipitation, the salt of formula I may also be recovered by lyophilization of the solution prepared in Step (1).

An alternative process for preparing the compounds of formula I comprises
1. forming a suspension of the amphoteric cephalosporin or a solvate or hydrate thereof in a suitable inert organic solvent, said solvent being a solvent for the triethylamine salt of the aldehyde reaction product of the amphoteric cephalosporin and a non-solvent for the alkali metal salt of formula I;
2. treating the suspension with the aldehyde and sufficient triethylamine to form in solution the triethylamine salt of the aldehyde reaction product of the amphoteric cephalosporin; and
3. precipitating the desired alkali metal salt of formula I from the solution by adding a solvent-soluble sodium or potassium base.

The starting material is slurried in an inert organic solvent which is a solvent for the triethylamine salt of the aldehyde reaction product of the amphoteric cephalosporin but which is an non-solvent for the desired alkali metal salt of formula I. The solvent selected for Step (1) should preferably be easily removable from the end-product under conditions which will not result in any appreciable decomposition of the end-product. Appropriate solvents for Step (1) may be determined by simple test.

The suspension formed in Step (1) is then treated with an aldehyde, preferably with a molar excess and most preferably with from about 1.3 to 1.4 moles of the aldehyde per mole of cephalosporin starting material, and sufficient triethylamine to form in solution the triethylamine salt of the cyclic reaction product of the aldehyde and the amphoteric cephalosporin. The reaction mixture is preferably stirred for at least about 30 minutes to ensure complete reaction. The amount of triethylamine used is not critical but preferably about 1 mole is used per mole of cephalosporin starting material. The reaction of Step (2) is conveniently done at room temperature but temperature higher or lower than this may be selected with the expected decrease or increase, respectively, in reaction time.

After formation of a solution or near-solution in Step (2), the reaction mixture is preferably carbon-treated and filtered as in the first-mentioned process discussed above.

The desired alkali metal salt of formula I may then be recovered from the solution of Step (2) by addition of a solvent-soluble sodium or potassium salt. The preferred salts are sodium or potassium salts of organic acids having between about 2 and 18 carbon atoms, e.g. solvent-soluble salts of such acids as 2-ethylhexanoic, caproic, oleic, glycolic, propionic, acetic, etc. Preferred salts for the methanol solvent system are sodium or potassium 2-ethylhexanoate, most preferably solutions of these salts in a methanolmiscible organic solvent such as acetone or isopropanol. The most preferred alkali metal salts are solutions of sodium or potassium 2-ethylhexanoate in isopropanol. The alkali metal salt is added, preferably slowly and with stirring, in sufficient quantity so as to obtain the maximum amount of precipitate from the solution. After complete precipitation has been effected, the reaction mixture is stirred, preferably for at least about 1 hour, and then filtered. The precipitate is washed with an appropriate organic solvent, e.g. methanol, and dried by conventional procedures, e.g. vacuum-drying at 50°–56° C. for 24–48 hours or air drying at 60° C. for 48 hours.

The second process may also be carried out without use of the triethylamine in Step (2). In this modified procedure the suspension of the amphoteric cephalosporin or a solvate or hydrate thereof, preferably the methanol or propylene glycol solvate or sesquihydrate and most preferably the methanol solvate, is suspended in an inert organic solvent which is a non-solvent for the product of formula I, preferably methanol, and the suspension then treated with the aldehyde, preferably a molar excess, and a solvent-soluble sodium or potassium base, said base being added in an amount sufficient to raise the pH of the reaction mixture to between about 5.5 and 8. It is preferred to use as bases the sodium or potassium salts mentioned above as being preferred in the second process. In the modified process the cephalosporin starting material goes into solution and the insoluble alkali metal salt then precipitates out almost instantaneously. Since a solution is not obtained upon completion of the reaction, the reaction mixture is preferably stirred and heated to about 45°–50° C. for a period of time of up to several hours to ensure maximum yields of end-product. The solid product is removed by filtration, washed and dried to give the desired salt of formula I.

The alkali metal salts of the present invention may be used to provide pharmaceutical formulations of the amphoteric cephalosporin which have acceptable thermal stability in the solid state, high solubility in water, satisfactory aqueous stabiliy, little or not muscle or vein irritation upon intravenous or intramuscular injection and excellent in vivo and in vitro antibacterial activity against a variety of Gram-positive and Gram-negative bacteria.

The sodium and potassium salts of formula I may be dissolved in water to form relatively concentrated solutions of at least 250 mg./ml. of activity. Concentrations of 250 mg./ml. of activity (pH 5.7–6.8) of these salts have acceptable aqueous stabilities.

In dilute aqueous solution the compounds of the present invention hydrolyze to the parent amphoteric cephalosporin of formula I. In acidic aqueous solutions at any concentration the compounds of this invention hydrolyze rapidly to said parent cephalosporin. This property makes them useful for purposes of purification of the parent amphoteric antibiotic, e.g. in solid from they can be washed with non-aqueous solvents to remove impurities soluble in such solvents and after such treatment are easily reconverted to the parent amphoteric antibiotic.

Activities of the compounds of formula I are substantially equivalent to those of the parent amphoteric cephalosporin.

In another aspect the present invention provides a pharmaceutical composition suitable upon reconstitution with water for use as a parenterally-administratable antibiotic formulation, said composition comprising a compound of formula I and a solid pharmaceutically acceptable water-soluble organic acid, said organic acid being present in an amount such that the pH of the fomulation upon reconstitution with water is between about 5.5 and 7.5.

The dry mixture of salt of formula I and organic acid in the above-mentioned composition may be reconstituted with water to provide a high concentration, i.e. up to at least 250 mg./ml., solution suitable for parenteral administration. The composition provided by the present invention may also be prepared by admixing a compound of formula I with a sufficient amount of a pharmaceutically acceptable water-soluble solid organic acid such that the pH of the composition upon reconstitution with water is between about 5 and 6.

The organic acid used in the composition may be any non-toxic, water-soluble, solid organic acid. Examples of suitable acids include citric, tartaric, glycine hydrochloride, ascorbic, succinic, and the like. The most preferred acid for use in the composition of the present invention is citric acid.

The exact proportions of compound of formula I and solid organic acid are dependent on the physical and chemical properties of the acid selected, e.g. acidity, solubility, etc. Generally it is found that the desired pH range of 5–6 upon reconstitution with water is achieved when the solid organic acid is used in an amount of about 4–6% of the weight of the compound of formula I.

The compounds of formula I as well as the above-mentioned compositions are potent antibacterial agents useful by both oral and parenteral administration in the treatment of infectious diseases in poultry and animals, including man, caused by many Gram -positive and Gram-negative bacteria. The compounds and compositions are also of value as nutritional supplements in animal feeds and as agents for the treatment of mastitis in cattle.

The salts and salt-organic acid mixtures of the present invention may be formulated as pharmaceutical compositions containing in addition to the active ingredient a pharmaceutically acceptable carrier or diluent. The compounds may be administered either orally or parenterally, but because of their high solubility in water, are especially useful for parenteral administration. In the treatment of bacterial infections in man, the compounds and compositions may be administered in an amount of from about 5 to 20 mg./kg./day in divided dosage, e.g. 3 to 4 times a day. They are administered in dosage units containing, e.g. 125, 250 or 500 mg. of active ingredient.

PREPARATION OF STARTING MATERIALS

The compounds of the present invention are prepared by reaction of an aldehyde having the structure $R^2$—CHO (wherein $R^2$ is as defined above) with a cephalosporin having the formula

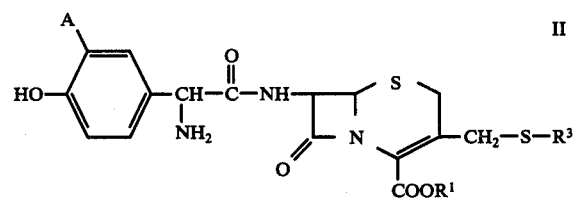

wherein A, $R^1$ and $R^3$ have the meaning set forth above. In the preferred embodiments the carbon bearing the α-amino group has the D configuration. The latter compounds are prepared by the general, and often specific, procedures set forth in the following patents:

U.S. Pat. No. 3,641,021
U.S. Pat. No. 3,855,213
U.S. Pat. No. 3,867,380
South Africa Pat. No. 73/4055
Belgium Pat. No. 776,222 (Farmdoc 38983T)
Belgium Pat. No. 810,477
West Germany Pat. No. 2,404,592 (Farmdoc 57268V)

An alternative method of preparing the amphoteric cephalosporins used as starting materials herein consists of substituting the appropriate p-hydroxy-2-phenylglycine (which may contain an additional substituent and in which the α-amino group is suitably protected during acylation in a conventional manner) for the side-chain acid, e.g. 2-phenylglycine or tetrazoleacetic acid, previously used to make either 3-thiolated cephalosporins or to make 7-substituted cephalosporanic acids in which the 3-acetoxy group is then displaced by the desired thiol. For examples see U.S. Pat. Nos. 3,757,012 and 3,757,015.

Reference below to BL-S643 refers to 7-[D-α-amino-α-(p-hydroxyphenyl)acetamido-3-(2-methyl-1,3,4-thiadiazol-5-yl-thiomethyl)-3-cephem-4-carboxylic acid which is also known as cefaparole.

The following examples are given in illustration of, but not in limitation of, the present invention.

DESCRIPTION OF THE PREFERRED EMBODIMENTS

EXAMPLE 1

Preparation of BL-S1057; The Sodium Salt Of the Reaction Product of BL-S643 and 2-Furaldehyde Formula, BL-S1057

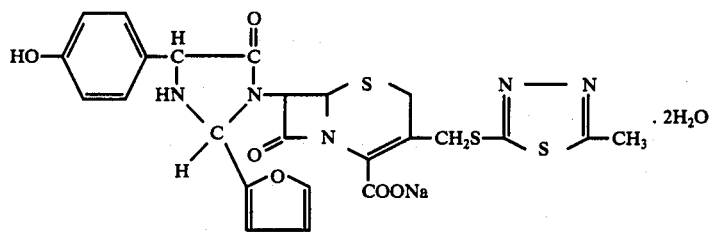

Procedure

1. Slurry 1 gram of BL-S643.3H$_2$O in 10 ml. of water at 40°–45° C.
2. Add 0.25 gram (1.25 equivalents) of 2-furaldehyde.
3. Add 1N sodium hydroxide with rapid stirring to pH 7–7.5. A solution or near solution is obtained in under 5 minutes.
4. Cool the solution to 22°–24° C. and suitably filter to remove particles, bacteria and pyrogens.
5. Lyophilize under sterile conditions for 48 hours to obtain BL-S1057 powder (BL-S1057 may also be obtained by precipitation of the sterile solution of step 4 with 15 to 20 volumes of sterile isopropanol).

Properties of BL-S1057 a. Bio-assay (using cefatrizine as the standard) = 759 mcg./mg.
b. IR = Intact β lactam; well-defined
c. NMR =
  1. Well-defined; consistent
  2. Approximately 75% cyclic adduct (60 mg./ml. in D$_2$O)
d. Solubility = >400 mg./ml. in water
e. Paper strip chromatography = Primarily 1 zone at R$_f$ of BL-S643 at 37° C. at 0 and 1 hour (concentration = 0.2 mg./ml.)
f. Liquid chromatography = 100% hydrolyzed in pH 6.1 buffer within 1 hour at room temperature (concentration = 1 mg./ml.)
g. MP = 180° C. (shrink) - 200° C. decomposes

| Analytical Data | | | | |
|---|---|---|---|---|
| | | Found | Dry Basis | Theory |
| % | H$_2$O KF | 5.18 | — | — |
| % | C | 45.91 | 48.4 | 48.4 |
| % | H | 4.05 | 3.7 | 3.37 |
| % | N | 10.81 | 11.4 | 11.8 |
| % | S | 14.92 | 15.73 | 16.48 |
| % | Ash as Na | 3.84 | 4.03 | 3.88 |

EXAMPLE 2

BL-S1058, the Reaction Product BL-S643 and Sodium-5-Formyl-2-Furansulfonic Acid

Formula, BL-S1058

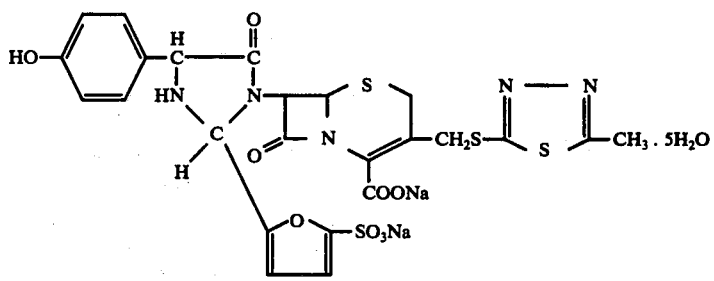

Preparation of BL-S1058

1. Slurry 0.45 gram of 5-formyl-2-furansulfonic acid sodium salt

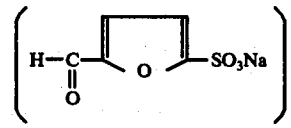

in 10 ml. of water at 40°–45° C. A solution or near solution is obtained.
2. Sprinkle in 1 gram of BL-S643.3H$_2$O over a 10 minutes period with rapid stirring and concomitant addition of 1N sodium hydroxide to pH 7–7.5. A solution or near solution is obtained within 5 minutes.
3. Cool to 20°–23° C. and pass the solution through suitable filters to remove particles, bacteria and pyrogens.
4. Lyophilize for 48 hours. The resulting powder is BL-S1058 (sterile BL-S1058 may also be obtained from the solution of step 3 by precipitation from 15-20 volumes of sterile isopropanol).

Properties of BL-S1058 a. Bio-assay (using cefatrizine as the standard) = 685 mcg./mg.
b. IR — NMR =
  1. Well-defined; consistent
  2. β-lactam and 3-side chain intact
  3. 90% cyclic adduct (at approximately 60 mg./ml. in D$_2$O).
c. Paper strip chromatography = Primarily 1 zone at R$_f$ of BL-S643 at 0 and 1 hour at 37° C. (concentration is 0.2 mg./ml.) There is evidence of a second zone.

d. Liquid chromatography (1 mg./ml. in pH 6 buffer)

| Time in Hours | % Hydrolyzed |
|---|---|
| 0 | 25.4 |
| 1 | 46.5 |
| 2 | 59.0 |

Analytical Data

| % | | Found | Dry Basis | Theory |
|---|---|---|---|---|
| % | H₂O KF | 10.17 | — | — |
| % | C | 36.5 | 40.5 | 41.6 |
| % | H | 2.89 | 2.4 | 2.74 |
| % | N | 8.52 | 9.49 | 10.01 |
| % | S | 17.09 | 18.98 | 18.6 |
| % | Ash as Na. | 7.04 | 7.93 | 6.63 |

| Antibiotic Spectrum of BL-S643 Derivatives in Nutrient Broth | | | | | |
|---|---|---|---|---|---|
| | | | MIC (mcg./ml.) | | |
| Organism | | | BL-S1057[(1)] | BL-S1058[(2)] | BL-S643 |
| S. pneumoniae* | $(10^{-3})$** | A9585 | 0.016 | 0.016 | 0.03 |
| Str. pyogenes* | $(10^{-3})$** | A9604 | 0.008 | 0.008 | 0.016 |
| S. aureus Smith | $(10^{-4})$ | A9537 | 0.5 | 0.25 | 0.5 |
| S. aureus +50% serum | $(10^{-4})$ | A9537 | 8 | 8 | 8 |
| S. aureus BX1633 | $(10^{-3})$ | A9606 | 1 | 0.5 | 1 |
| S. aureus BX1633 | $(10^{-2})$ | A9606 | 4 | 4 | 4 |
| S. aureus Meth-Res | $(10^{-3})$ | A15097 | 2 | 2 | 4 |
| Sal. enteritidis | $(10^{-4})$ | A9531 | 0.25 | 0.13 | 0.25 |
| E. coli Juhl | $(10^{-4})$ | A15119 | 1 | 1 | 1 |
| E. coli | $(10^{-4})$ | A9675 | 4 | 2 | 4 |
| K. pneumoniae | $(10^{-4})$ | A9977 | 0.5 | 0.5 | 0.5 |
| K. pneumoniae | $(10^{-4})$ | A15130 | 4 | 2 | 4 |
| Pr. mirabilis | $(10^{-4})$ | A9900 | 0.5 | 0.5 | 0.5 |
| Pr. morganii | $(10^{-4})$ | A15153 | 16 | 16 | 16 |
| Ps. aeruginosa | $(10^{-4})$ | A9843A | >125 | >125 | >125 |
| Ser. marcescens | $(10^{-4})$ | A20019 | 125 | 125 | 125 |
| Ent. cloacae | $(10^{-4})$ | A9656 | >125 | >125 | >125 |
| Ent. cloacae | $(10^{-4})$ | A9657 | 0.5 | 0.5 | 4 |
| Ent. cloacae | $(10^{-4})$ | A9659 | 16 | 16 | 32 |

*45% AAB + serum + 50% broth listed above.

R = 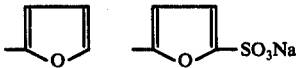

**Dilution of overnight broth culture.

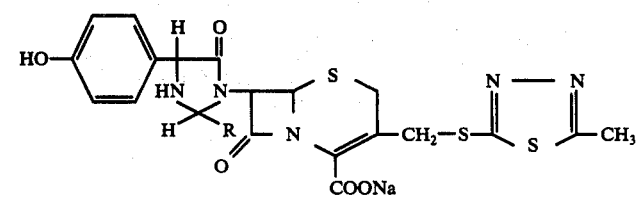

[(1)]Adjusted for 80% content of BL-S643.
[(2)]Adjusted for 59% content of BL-S643.
In other words, the numerical values are lowered, i.e. improved. This adjustment was also made in the tests reported below or in the alternative, a larger weight was used to equivalent dosage.

Paper chromatograms were run on rat urine collected between 0 and 2 and between 2 and 4 hours following IM administration of BL-S1057, 1058 and 643, for the detection of antibiotically active metabolites using descending chromatography with system No. 9 (butyl acetaten-butanol:glacial acetic acid:H₂O = 80:15:40:24). A single, identical spot was observed in all cases. This indicates complete hydrolysis of the two derivatives to the parent compound (BL-S643).

EXAMPLE 3

Compounds of the formula

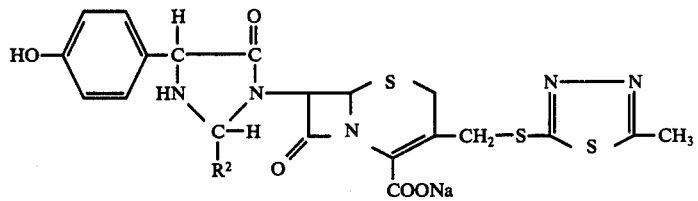

wherein R² is phenyl-2-sulfonic acid, 4-methoxyphenyl-3-sulfonic acid, 4-hydroxyphenyl-3-sulfonic acid, 2-carboxymethoxyphenyl, 4-carboxymethoxyphenyl, 3-hydroxy-4-carboxyyphenyl, 4-(2'-carboxy)vinylphenyl, carboxyl, 2-carboxyphenyl, 3-carboxyphenyl, methanesulfonic acid, and methanedisulfonic acid respectively are prepared by replacing the 5-formyl-2-furansulfonic acid in the procedure of Example 2 with an equimolar weight of the corresponding aldehyde having the formula R²—CHO.

EXAMPLE 4

The compounds having the formulae

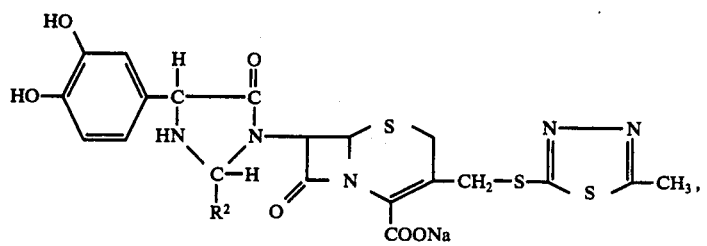
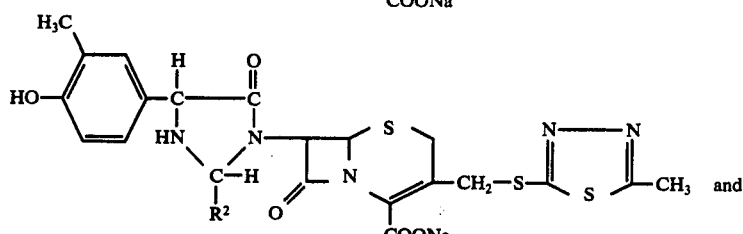
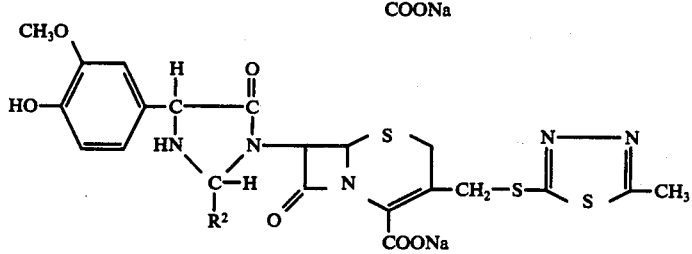
wherein R² is
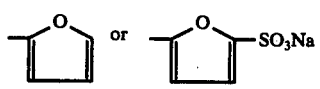
are prepared by substituting an equimolar weight of the corresponding amphoteric cephalosporin for the cefaparole in the procedures of Examples 1 and 2.
EXAMPLE 5
The compounds having the formulae
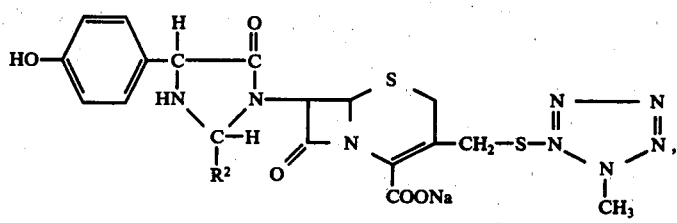
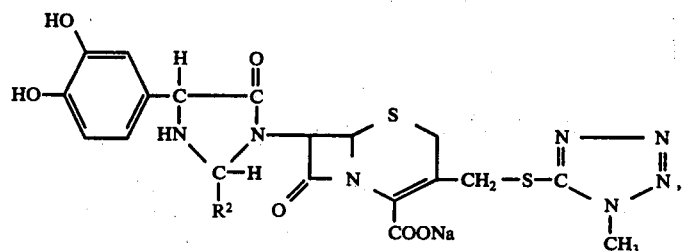
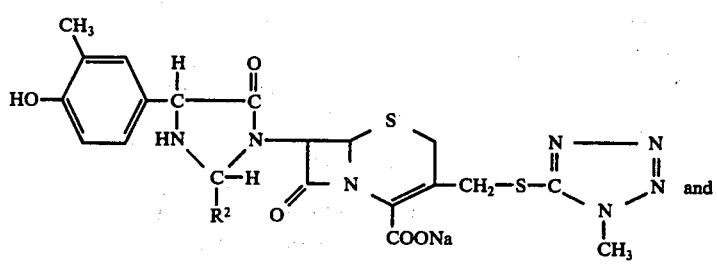

-continued

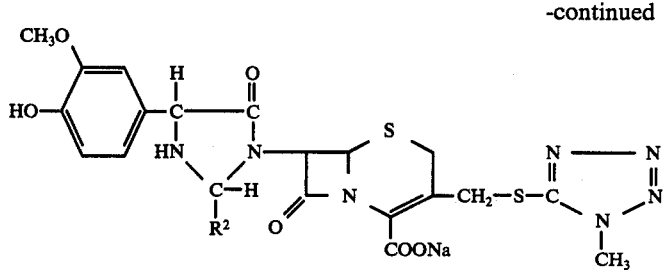

| wherein R² is | wherein R² is |
|---|---|
|  |  |
| are prepared by substituting an equimolar weight of the corresponding amphoteric cephalosporin for the cefaparole in the procedures of Examples 1 and 2. | are prepared by substituting an equimolar weight of the corresponding amphoteric cephalosporin for the cefaparole in the procedures of Examples 1 and 2. |
| EXAMPLE 6 | EXAMPLE 7 |
| The compounds having the formulae | The compounds having the formulae |

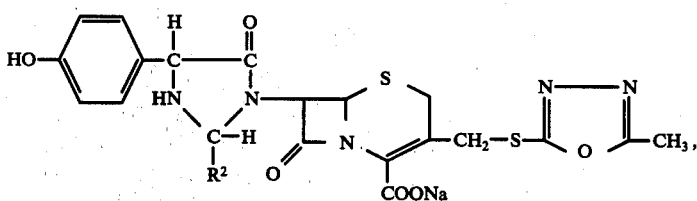

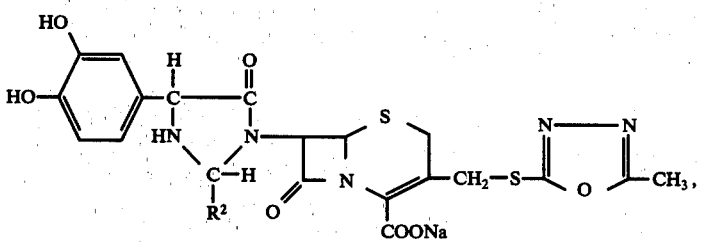

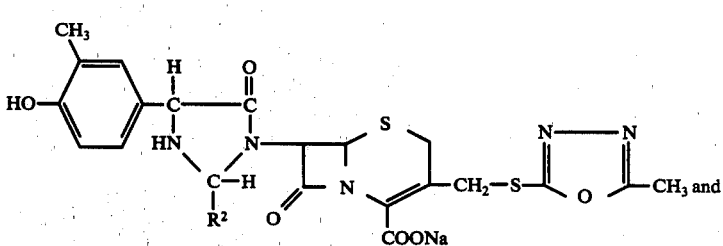

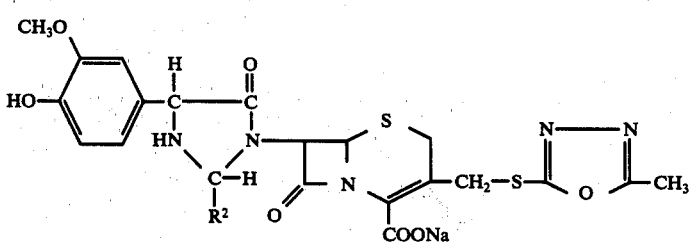

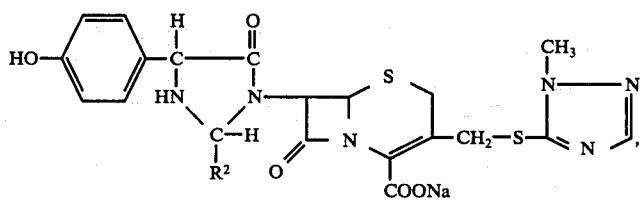
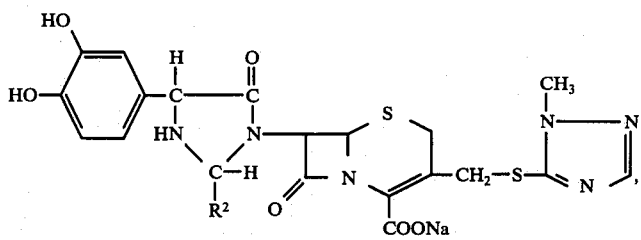
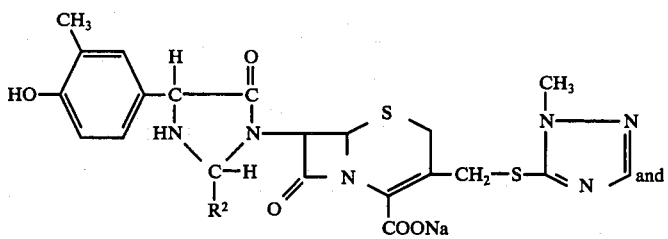
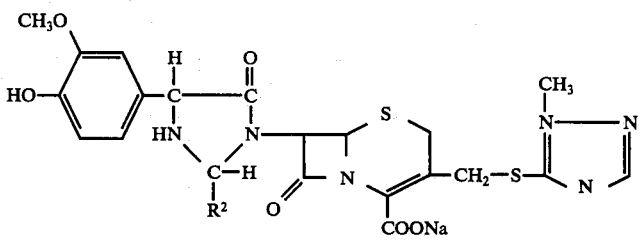
wherein R² is
are prepared by substituting an equimolar weight of the corresponding amphoteric cephalosporin for the cefaparole in the procedures of Examples 1 and 2.
EXAMPLE 8
The compounds having the formulae
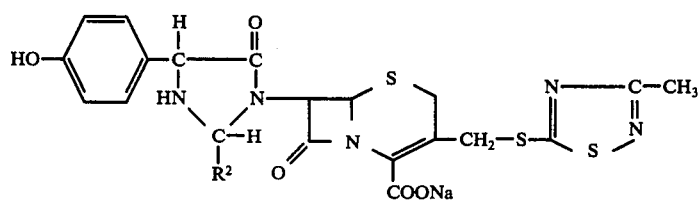
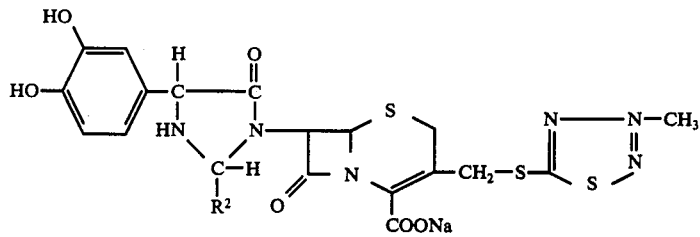

-continued
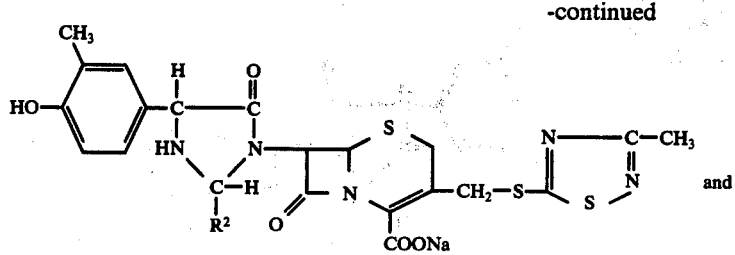
and
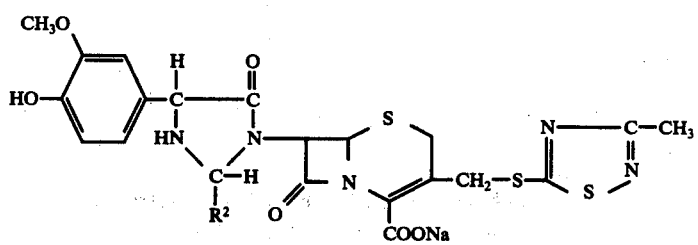
wherein R² is
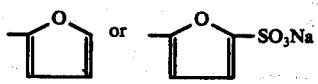
are prepared by substituting an equimolar weight of the corresponding amphoteric cephalosporin for the cefaparole in the procedures of Examples 1 and 2.
EXAMPLE 9
The compounds having the formulae
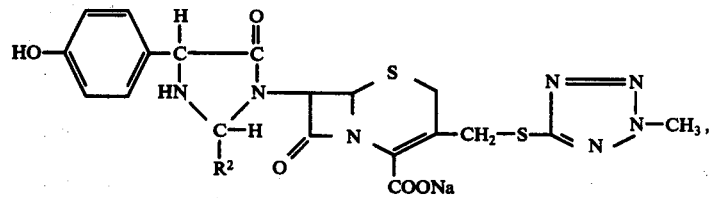
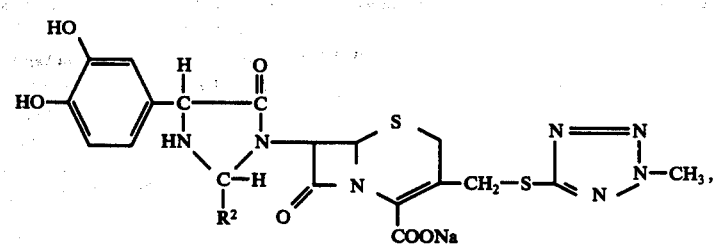
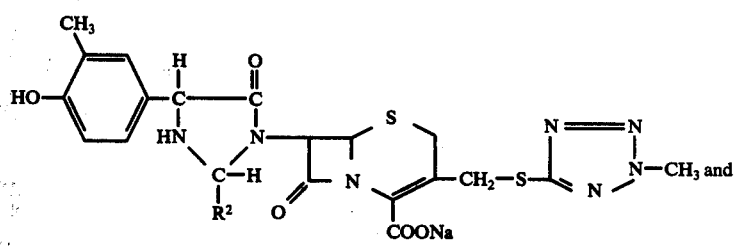
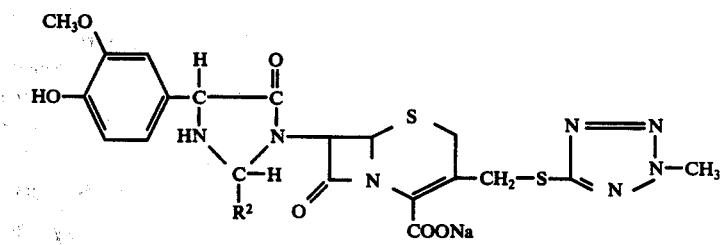
wherein R² is
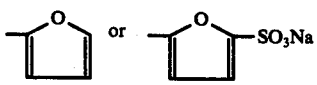

are prepared by substituting an equimolar weight of the corresponding amphoteric cephalosporin for the cefaparole in the procedures of Examples 1 and 2.

We claim:
1. A compound of the formula

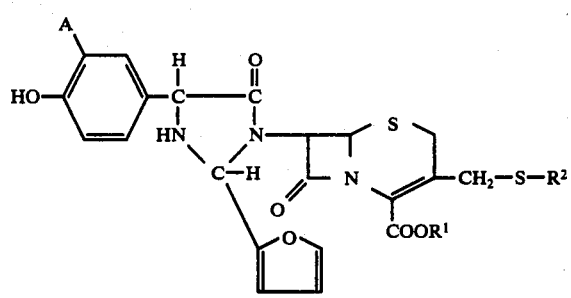

wherein
A is hydrogen, hydroxy, methyl or methoxy,
$R^1$ is hydrogen, sodium or potassium, and
$R^2$ is tetrazol-5-yl, 1,2,4-thiadiazol-5-yl, 1,3,4-thiadiazol-2-yl, 1,3,4-oxadiazol-3-yl or 1,2,4-triazol-5-yl, each of such groups being unsubstituted or substituted with one or two lower alkyl groups of one to four carbon atoms.

2. A compound of the formula

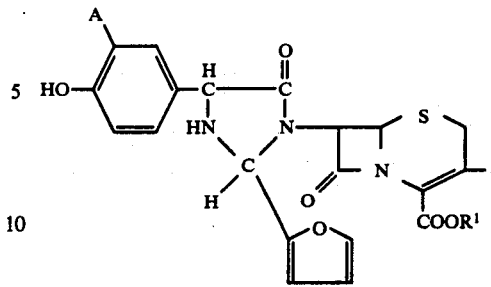

$$-CH_2S-\underset{S}{\overset{N \longrightarrow N}{\Big\langle \quad \Big\rangle}}-CH_3$$

wherein
A is hydrogen, hydroxy, methyl or methoxy, and
$R^1$ is hydrogen, sodium or potassium.

3. A compound of the formula

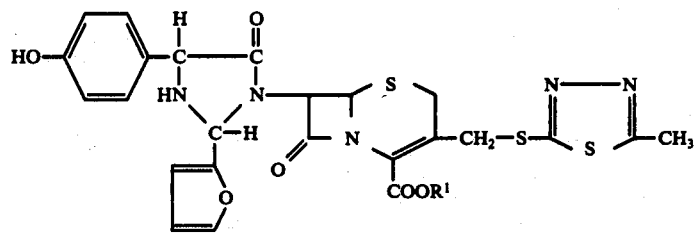

wherein
$R^1$ is hydrogen, sodium or potassium.

4. The compound of claim 3 having the D configuration wherein $R^1$ is sodium.

5. The compound of claim 3 having the D configuration wherein $R^1$ is potassium.

6. The compound of claim 3 having the D configuration wherein $R^1$ is hydrogen.

7. A compound of the formula

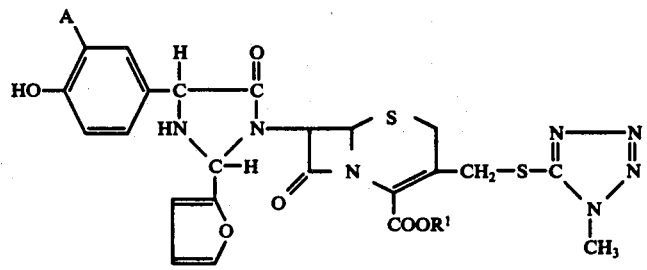

wherein
A is hydrogen, hydroxy, methyl or methoxy and
$R^1$ is hydrogen, sodium or potassium.

8. A compound of claim 7 of the formula

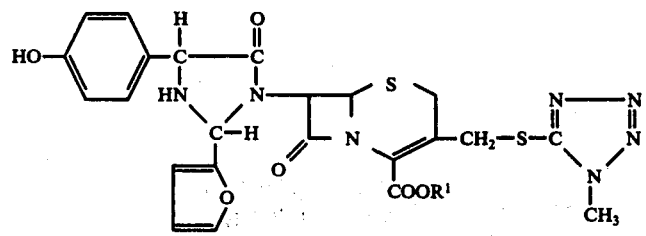

wherein
R¹ is hydrogen, sodium or potassium.
9. The compound of claim 8 having the D configuration wherein R¹ is sodium.
10. The compound of claim 8 having the D configuration wherein R¹ is potassium.
11. The compound of claim 8 having the D configuration wherein R¹ is hydrogen.
12. A compound of the formula

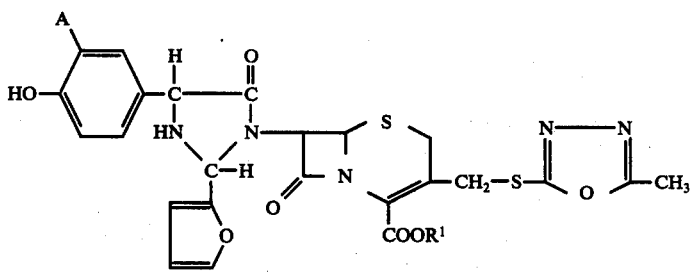

wherein
A is hydrogen, hydroxy, methyl or methoxy and R¹ is hydrogen, sodium or potassium.
13. A compound of claim 12 of the formula

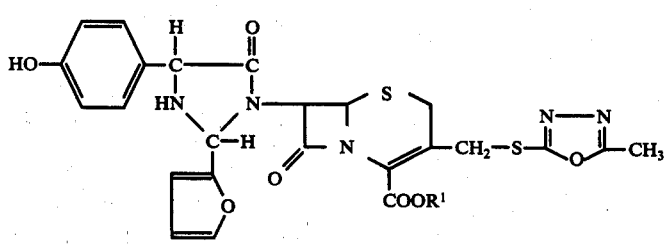

wherein
R¹ is hydrogen, sodium or potassium.
14. The compound of claim 13 having the D configuration wherein R¹ is sodium.

15. The compound of claim 13 having the D configuration wherein R¹ is potassium.
16. The compound of claim 13 having the D configuration wherein R¹ is hydrogen.
17. A compound of the formula

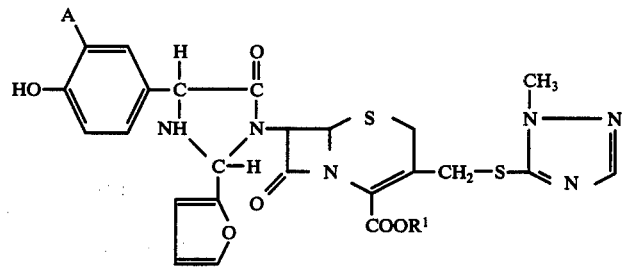

wherein:
A is hydrogen, hydroxy, methyl or methoxy and R¹ is hydrogen, sodium or potassium.
18. A compound of claim 17 of the formula

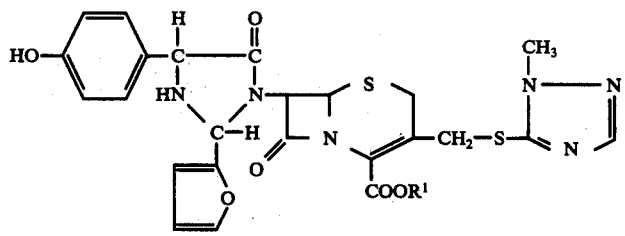

wherein
R¹ is hydrogen, sodium or potassium,
19. The compound of claim 18 having the D configuration wherein R¹ is sodium.
20. The compound of claim 18 having the D configuration wherein R¹ is potassium.
21. The compound of claim 18 having the D configuration wherein R¹ is hydrogen.
22. A compound of the formula

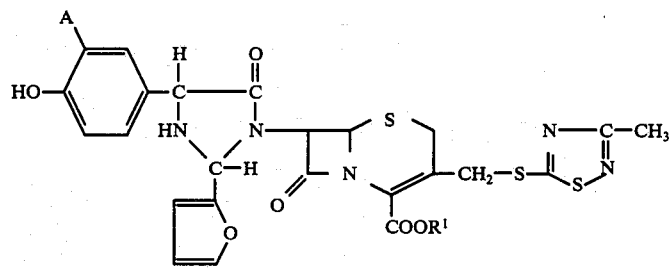

wherein
A is hydrogen, hydroxy, methyl or methoxy and
R¹ is hydrogen, sodium or potassium.
23. A compound of claim 22 of the formula

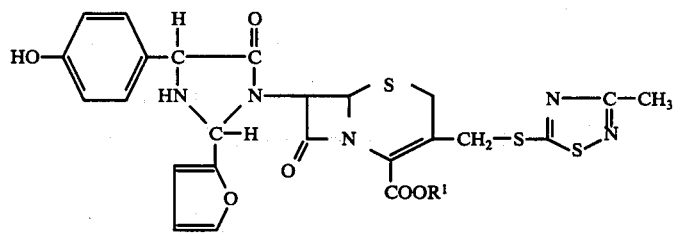

wherein
R¹ is hydrogen, sodium or potassium.
24. The compound of claim 23 having the D configuration wherein R¹ is sodium.
25. The compound of claim 23 having the D configuration wherein R¹ is potassium.
26. The compound of claim 23 having the D configuration wherein R¹ is hydrogen.
27. A compound of the formula

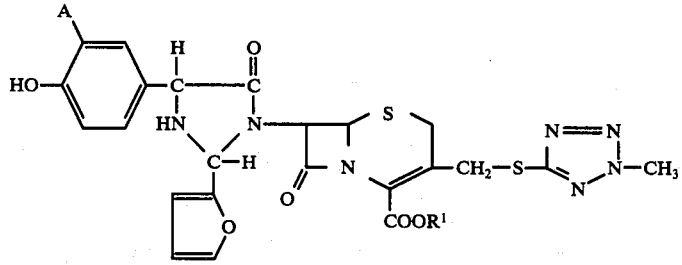

wherein
A is hydrogen, hydroxy, methyl or methoxy and
R¹ is hydrogen, sodium or potassium.
28. A compound of claim 27 of the formula

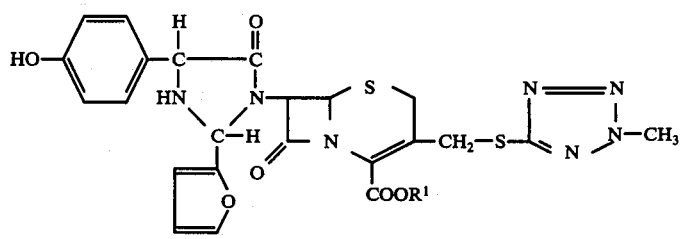

wherein
R¹ is hydrogen, sodium or potassium.
29. The compound of claim 28 having the D configuration wherein R¹ is sodium.
30. The compound of claim 28 having the D configuration wherein R¹ is potassium.
31. The compound of claim 28 having the D configuration wherein R¹ is hydrogen.

* * * * *